(12) United States Patent
Saurel

(10) Patent No.: US 9,158,011 B2
(45) Date of Patent: Oct. 13, 2015

(54) IN SITU SYSTEM FOR DIRECT MEASUREMENT OF ALPHA RADIATION, AND RELATED METHOD FOR QUANTIFYING THE ACTIVITY OF ALPHA-EMITTING RADIONUCLIDES IN SOLUTION

(75) Inventor: Nicolas Saurel, Varois et Chaignot (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 252 days.

(21) Appl. No.: 13/877,404

(22) PCT Filed: Oct. 7, 2011

(86) PCT No.: PCT/EP2011/067578
§ 371 (c)(1),
(2), (4) Date: Apr. 2, 2013

(87) PCT Pub. No.: WO2012/045870
PCT Pub. Date: Apr. 12, 2012

(65) Prior Publication Data
US 2013/0200267 A1 Aug. 8, 2013

(30) Foreign Application Priority Data
Oct. 7, 2010 (FR) ...................................... 10 58151

(51) Int. Cl.
*G01T 1/24* (2006.01)
(52) U.S. Cl.
CPC ............ *G01T 1/24* (2013.01); *G01N 2223/626* (2013.01)
(58) Field of Classification Search
CPC .............................. G01T 1/24; G01N 2223/626

USPC .................................................... 250/370.02
See application file for complete search history.

(56) References Cited

U.S. PATENT DOCUMENTS

| 5,689,115 A | 11/1997 | Balan et al. |
| 6,369,389 B1 | 4/2002 | Berland et al. |

(Continued)

FOREIGN PATENT DOCUMENTS

| DE | 196 48 211 A1 | 5/1997 |
| GB | 1 253 636 | 11/1971 |
| GB | 2 404 780 A | 2/2005 |

OTHER PUBLICATIONS

International Search Report issued Jan. 31, 2012 in Application No. PCT/EP2011/067578.

(Continued)

*Primary Examiner* — David Porta
*Assistant Examiner* — Faye Boosalis
(74) *Attorney, Agent, or Firm* — Oblon, McClelland, Maier & Neustadt, L.L.P.

(57) ABSTRACT

A system for in situ nuclear measurement of alpha radiation of an effluent and a related method. The system includes: M diamond semiconductor detectors obtained by chemical vapor deposition, or silicon semiconductor detectors covered with a diamond layer, as alpha radiation detectors, configured to be immersed in the effluent, and to measure alpha radiation emitted by the effluent, M is an integer greater than or equal to 1; P measuring channels connected to the M alpha radiation detectors, P is an integer greater than or equal to 1 and less than or equal to M, each of the P measuring channels configured to provide a value or a sum of alpha activity values from the M alpha radiation detectors to which they are connected; and, if P is greater than 1, a mechanism for adding together results from the P measuring channels.

21 Claims, 2 Drawing Sheets

(56) References Cited

U.S. PATENT DOCUMENTS

2009/0057545 A1* 3/2009 Saenger et al. ............ 250/269.4
2010/0155615 A1* 6/2010 Whitehead et al. ...... 250/370.14

OTHER PUBLICATIONS

Database Compendex [online], "Monte-Carlo computation of the calibration factor of solid state nuclear track detector for radon and the effect by atmospheric pressure", Data Accession No. E2004258227139, XP-002638757, vol. 38, No. 1, Jan. 2004, 1 page.
P. Vojtyla, "Calibration of monitors used for surveillance of radioactivity in effluent water from CERN's accelerator installations", Applied Radiation and Isotopes, vol. 55, 2001, pp. 81-88.
H.A. Khan, et al., "SSNTD Applications in Science and Technology—A Brief Review", Radiation Measurements, vol. 31, 1999, pp. 25-36.

* cited by examiner

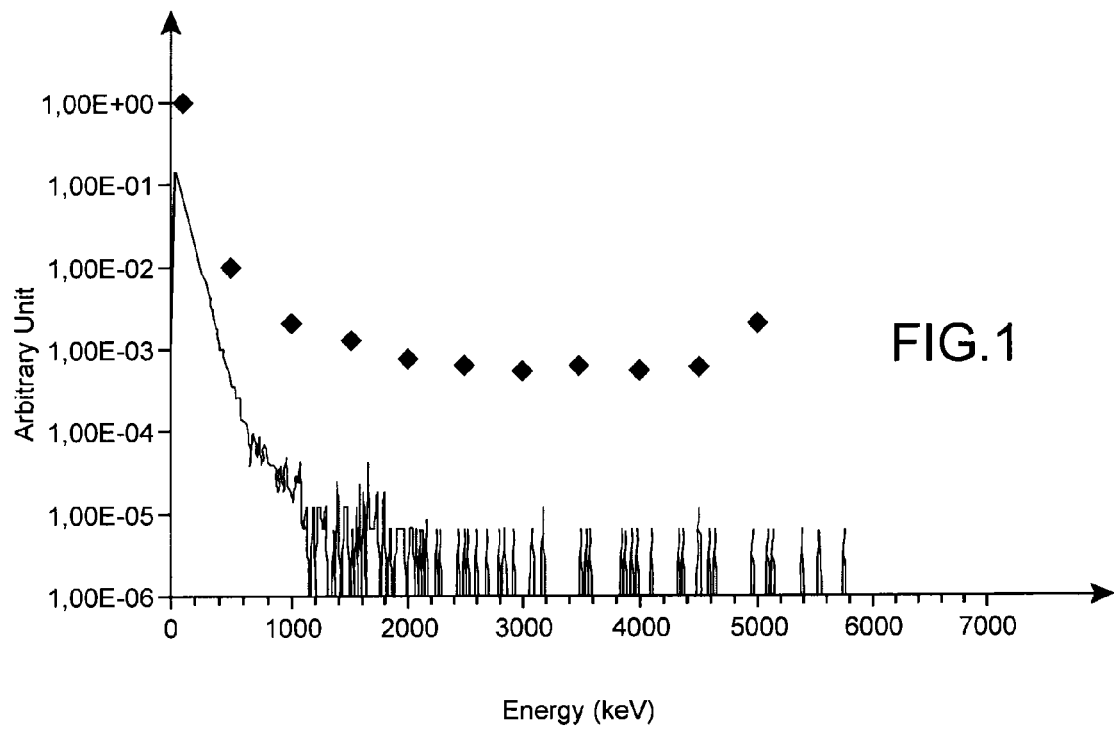
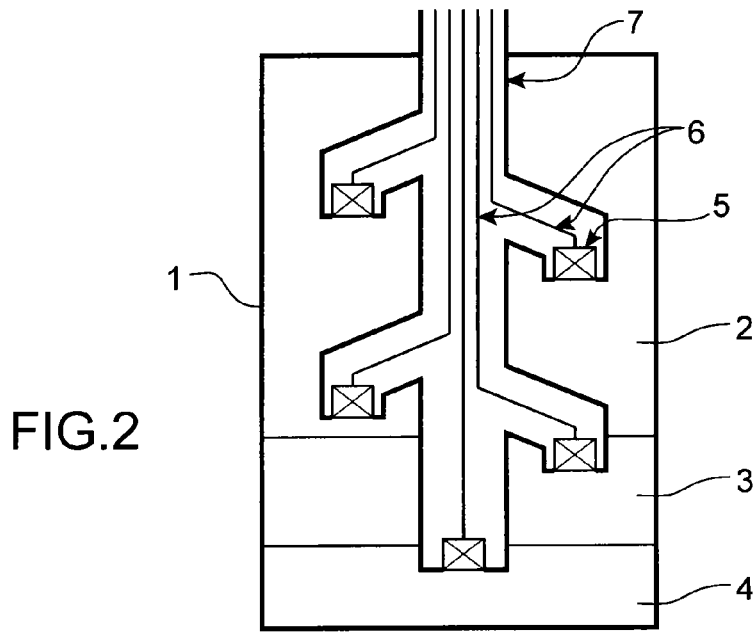

IN SITU SYSTEM FOR DIRECT MEASUREMENT OF ALPHA RADIATION, AND RELATED METHOD FOR QUANTIFYING THE ACTIVITY OF ALPHA-EMITTING RADIONUCLIDES IN SOLUTION

TECHNICAL FIELD

The invention relates to in situ quantification of the activity of the alpha-emitting radionuclides present in an effluent by a system of non-destructive measurement of the alpha radiation, and its related measuring method.

STATE OF THE PRIOR ART

The subject is the quantification of the activity of the alpha-emitting radioelements contained in certain effluents by measuring the alpha radiation emitted by these effluents. This quantification is required to accomplish the material monitoring (safety aspect) and to treat the effluent (for example, in order to determine whether the effluent can or cannot be transported to a reprocessing centre, which reprocessing channel is appropriate, etc.).

It is specified that one definite interest of alpha radiation measurement, compared to gamma radiation measurement, is that it has a much lower detection limit, and that it avoids complex attenuation corrections.

It is also recalled that the term "effluent" designates all liquid discharges conveying a polluting load (whether dissolved or in the form of particles) which is harmful to the environment. Effluents encompass, for example, all waste water, whether or not treated, deriving from a water treatment plant (for example, drainage water and industrial discharges). It is recalled that the orders of magnitude sought for such quantifications vary from several hundred $Bq/m^3$ to $1.10^5$ $Bq/m^3$ for the U, Pu and Am radionuclides.

Alpha activity of effluents is currently quantified in several steps: taking an effluent sample volume, transporting this sample to an analysis laboratory and, after arriving at the laboratory, sampling a portion of the sample volume in order to analyse it. Analysis is undertaken by cupellation drying. It is recalled that cupellation drying consists in evaporating a liquid by heating. The residues deposited on the cupel at the end of the operation are measured, and the alpha activity of the residues is quantified, for example by using a detector of the grid counter type, or a semiconductor detector of the PIPS (Passivated Implanted Planar Silicon) silicon type. This method generally involves the use of a radioactive tracer, which implies that reference nuclear materials are supplied, and that additional nuclear waste is generated.

The disadvantage of this procedure is that it requires an effluent sample. The measuring method is therefore destructive.

In addition, this procedure requires that several operators intervene to take the sample, transport it and analyse it.

The inventor therefore aimed to design a system and a measuring method enabling the alpha activity of an effluent to be quantified in a non-destructive and in situ manner, in solution.

DESCRIPTION OF THE INVENTION

This aim is achieved by virtue of a system for in situ nuclear measurement of the alpha radiation of an effluent, including:
  M diamond semiconductor detectors of the CVD (Chemical Vapour Deposition) type, or silicon detectors covered with a diamond layer and made opaque to visible light (i.e. for a wavelength of between 400 and 800 nm), called alpha radiation detectors, intended to be immersed in the effluent, and able to measure the alpha radiation emitted by said effluent, where M is an integer greater than or equal to 1;
  P measuring channels connected to the M alpha radiation detectors, where P is an integer greater than or equal to 1 and less than or equal to M, and where each of the P measuring channels is able to supply an alpha activity value or a sum of such values from the alpha radiation detector(s) to which they are connected;
  wherein the system also includes, if P is greater than 1, a means for adding together the results from the P measuring channels, and wherein the M alpha radiation detectors are individually calibrated by an α particle transport code based on the Monte Carlo method, the alpha radiation detectors connected to a given measuring channel being calibrated in the same manner.

The diamond semiconductor detectors of the CVD type or silicon semiconductor detectors covered with a diamond layer are respectively diamond detectors obtained by chemical vapour deposition, or silicon detectors of the monocrystalline or polycrystalline SOI (Silicon On Insulator) type on which a diamond layer obtained by chemical vapour deposition has been deposited. These can under no circumstances be detectors which are non-selective with regard to alpha radiation. For example, a gamma radiation detector of the HPGe type (Hyper Pure Germanium) would not be suitable.

The principle of α particle detection is the formation, in a semiconductor detector, of electron-hole pairs after the α particle's impact on the surface of the detector. The number of electron-hole pairs depends on the energy of the α particle, which enables an energy spectrum to be obtained. SOI (Silicon On Insulator) detectors and CVD (Chemical Vapour Deposition) detectors measure the residual energy deposited by the α particle.

The means for adding together the results from the P measuring channels may be, for example, a conventional scaler for multi-channel analysis. The M alpha radiation detectors are individually calibrated by an α particle transport code based on the Monte Carlo method, where the alpha radiation detectors connected to a given measuring channel are calibrated in the same manner. The Monte Carlo method is a statistical calculation method which, in this case, enables the calibration coefficients of the alpha radiation detectors to be determined digitally.

M is advantageously greater than or equal to 2. The measuring system then includes at least two alpha radiation semiconductor detectors.

P is advantageously equal to M. There are then as many measuring channels as alpha radiation detectors: each of the alpha radiation detectors is therefore calibrated individually. The gradient of the effluent's alpha activity may thus be obtained, together with a specific calibration according to the effluent phases, and the physical-chemical characteristics of each of the effluent's phases may be determined.

According to a particular variant of the invention, when the effluent has Q different phases, where Q is an integer greater than or equal to 2, at least two alpha radiation detectors are positioned in different phases of the effluent. Phases differ in terms of their physical-chemical nature, their density, salinity, etc. The measuring system advantageously has at least one alpha radiation detector for each effluent phase.

The M alpha radiation detectors are preferentially identical. This enables the results obtained by these M alpha radiation detectors to be compared directly, without having to perform additional calculations, for example to identify the presence of a gradient of activity.

According to a first variant, the measuring system according to the invention also includes a monocrystalline semiconductor detector, called a spectrometry detector, intended to be immersed in the effluent, and enabling the proportion of the alpha activity emitter elements present in the effluent to be identified and quantified.

The monocrystalline semiconductor detector is advantageously chosen from among a diamond CVD or SOI semiconductor detector. To identify and quantify the proportion of the alpha activity emitter elements a specific device is positioned in front of the detector. For example, the detector dedicated to spectrometry may be fitted with a channel which passes an effluent plate of micrometric thickness in front of the detector. Using the data supplied by this detector dedicated to spectrometry, the alpha activity of each alpha emitter element contained in the effluent may then be known.

According to a second variant, among the M alpha radiation detectors contained in the measuring system one alpha radiation detector is monocrystalline, and is connected to a first measuring channel, chosen from among the P measuring channels, which provides an alpha activity value and is connected to a second measuring channel, different from the P measuring channels, which provides the spectrometry of the effluent. In this particular case a single detector is used both as an alpha radiation detector and as a spectrometry detector. To have both these functions the detector will necessarily be a diamond monocrystalline or SOI semiconductor detector.

The measuring system according to the invention advantageously also includes holding means, enabling the M alpha radiation detectors to be held immersed in determined positions in the effluent.

The holding means advantageously hold at least two alpha radiation detectors at different heights in the effluent.

The means for holding the M alpha radiation detectors are advantageously a shaft (for example an axe), with branches at which the M alpha radiation detectors are positioned. The M alpha radiation detectors are advantageously located at the ends of the branches. There are preferably M branches.

The branches may preferably be moved on the shaft; the distance between the branches may thus be modified, and the alpha radiation detectors may thus be moved and attached at a more satisfactory height in the effluent.

According to one variant the spectrometry detector is attached to one of the holding means. If the holding means are a shaft with M branches this shaft may include an additional branch to which the monocrystalline spectrometry detector will be attached.

The monocrystalline or SOI diamond detector is preferably positioned in the upper portion of the volume of effluent, i.e. in the portion of the effluent having the fewest particles in suspension.

The invention also relates to a method for in situ nuclear measurement of the alpha radiation of an effluent. This measuring method includes the steps consisting in:

immersing in the effluent M diamond semiconductor detectors of the CVD type, or silicon semiconductor detectors covered with a diamond layer, able to measure the effluent's alpha activity, where M is an integer greater than or equal to 1, where the M alpha radiation detectors are connected to P measuring channels, where P is an integer greater than or equal to 1 and less than or equal to M, and where said M semiconductor detectors are called alpha radiation detectors;

calibrating the M alpha radiation detectors, where the detectors connected to a given measuring channel are calibrated in the same manner, and where the calibration is undertaken by an $\alpha$ particle transport code based on the Monte Carlo method;

detecting P values of the alpha radiation using the P measuring channels connected to said M alpha radiation detectors, where the $i^{th}$ value detected (where i=1 to P) is equal either to the value resulting from a single alpha radiation detector, if the corresponding measuring channel is connected only to said alpha radiation detector, or to the sum of the values from the alpha radiation detectors connected by said measuring channel, if P is greater than 1, adding together the P alpha radiation values.

If P is equal to M, the detected values are equal to the values obtained by the alpha radiation detectors, where each alpha radiation detector then has its own measuring channel: the values detected by the P measuring channels are then not sums of values from several alpha radiation detectors, but the values originating from each detector.

The M alpha radiation detectors are advantageously positioned at different heights in the effluent.

According to one variant, when the effluent has Q different phases, where Q is an integer greater than or equal to 2, at least two alpha radiation detectors are immersed in different phases. There is advantageously at least one alpha radiation detector for each different phase. The M detectors are thus positioned in such a way that there is at least one alpha radiation detector in each phase of the effluent.

The measuring method advantageously also includes a step consisting in performing a spectrometry of the effluent to determine the identity and proportion of the alpha emitter elements present in the effluent.

The step consisting in performing a spectrometry of the effluent is preferably undertaken by immersing a monocrystalline semiconductor detector or silicon detector covered with a diamond layer (diamond SOI) (i.e. a detector equipped, for example, with a micrometric channel) in the effluent, and by detecting the values supplied by said monocrystalline semiconductor detector or silicon detector covered with a diamond layer (diamond SOI).

The device and the method according to the invention enable quantification of the alpha emitters present in the radioactive effluents to be improved.

As was seen in the paragraph covering the prior art, the alpha emitters present in the effluents are currently quantified by taking a sample which is analysed by destructive methods. These methods have many disadvantages, namely the sampling, the transport of the radioactive sample, the requirement to have a nuclear-capable laboratory to undertake the analysis of the sample, the destructive analysis methodology, and the impossibility of such quantification when there are undesired radioactive emissions (due, for example, to caesium being present in large quantities), and finally management of the samples as nuclear waste.

The solution to resolve the problems of the prior art consists in directly immersing in the effluent to be characterised one or more alpha radiation sensors which are calibrated digitally, individually, specifically and following each modification of the physical-chemical properties of the effluent phase in which they are immersed, without removing said sensors from the effluent.

The originality of the invention is that it combines one or more alpha radiation detectors of the diamond CVD or SOI type, positioned in situ in the effluent (where the number of detectors can be adjusted according to the volume of effluent to be characterised and its heterogeneity), wherein coupling the detector or detectors to a measuring channel provides spectrometry of the alpha emitters present in the effluent, and quantification of the alpha emitters through a numerical calibration specific to each of the immersed detectors, without beforehand having to use a calibration source and to remove the sensor from the effluent in order to calibrate it. It is possible to calibrate the detectors due to the mean free path properties of the alpha particles in the effluent and the data accessible inline (salinity, pH, filling rate, number of phases present, etc.) concerning the effluent to be characterised.

The fact that there is specific calibration for each sensor notably enables the heterogeneous aspects of the effluent to be determined. Indeed, by positioning the sensors judiciously in the effluent the alpha emitters present in each effluent phase may be quantified.

The device and the method according to the invention have many advantages.

Firstly, they enable the activity of the alpha emitters to be quantified, even when other radionuclides are present, due to a better selectivity of the detectors used, namely of the diamond CVD or SOI detectors.

Secondly, an inline measurement (quantification and spectrometry) of the effluent's alpha radiation is obtained.

Improved performance is also obtained in terms of the lower limit of quantification and accuracy of measurement.

A device is obtained which is easier to maintain, which can easily be decontaminated and which is easily transportable, which is impossible with a gamma radiation measuring device.

The use of calibration sources generating additional radioactive waste is avoided, since the calibration is digital. Calibration according to the invention is effective and possible even when the effluent is very heterogeneous, since the detector may be moved to each phase of the effluent, or a detector may be positioned in each phase. It is also versatile, since it enables each modification of the physical-chemical characteristics of the effluent (addition of a new effluent to the tank, neutralisation of it, etc.) to be taken into account.

The device and the method according to the invention enable the alpha activity of the effluents to be quantified. They may, for example, be used to monitor the alpha activity of effluent, or again to activate operations when the effluent has the required quantity of alpha emitters.

BRIEF DESCRIPTION OF THE DRAWINGS

The invention will be better understood and other advantages and features will appear on reading the following description, which is given as a non-restrictive example, accompanied by the appended drawings, among which:

FIG. 1 represents the change in the signal-to-noise ratio as a function of energy for a semiconductor alpha radiation detector in water, FIG. 2 represents an example embodiment of the measuring system according to the invention.

Figure 3:
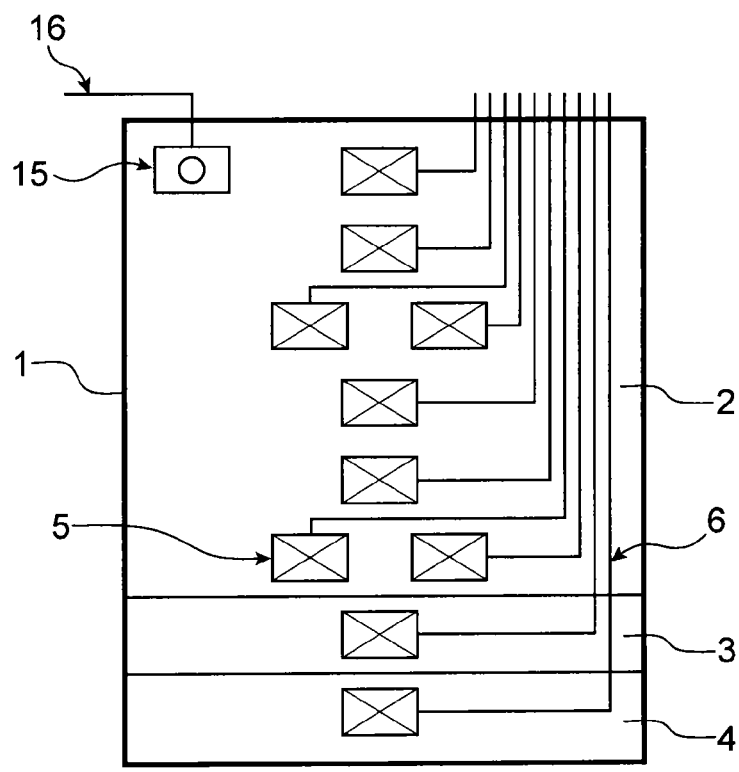
FIG. 3 represents another example embodiment of the measuring system according to the invention.

It is stipulated that the elements constituting the figures are not represented to scale.

DETAILED ACCOUNT OF PARTICULAR EMBODIMENTS

The measuring system according to the invention and the related method enable the activity of the alpha radioelements present in solution to be measured in situ and non-destructively.

The originality of the invention lies in the combination of nuclear measurements made using one or more alpha radiation semiconductor detectors of the diamond CVD or SOI type, made opaque to visible light (400-800 nm) and placed directly in the solution to be characterised (effluent), and determination of the calibration coefficient of said detector or detectors in digital fashion (by 3-D Monte Carlo calculation code for transport of the alpha particles). This combination enables an inline non-destructive measurement of the alpha activity of the radioelements present in the effluent, and in particular in all phases of the effluent (clean solutions and/or in the effluent's decantation sludges), to be obtained, when several detectors positioned in the different phases of the effluent are used, and thus enables the distribution of the radioelements in the effluent to be determined.

The measuring system and the related method not only allow the overall alpha activity of an effluent to be known, but they can also provide the alpha activity radioelement by radioelement when the measuring system includes a monocrystalline semiconductor detector of the diamond CVD or diamond SOI type dedicated to spectrometry. Such a monocrystalline semiconductor detector of the diamond CVD or SOI diamond type, in combination with a measuring channel enabling the effluent's spectrometric measurement to be made, enables the proportion of the radioelements present in the effluent to be known. This diamond monocrystalline or SOI semiconductor detector may possibly be used both for measuring the alpha activity and the spectrometry of the effluent.

In the invention, the calibration of the detector(s) dedicated to measuring the alpha activity is accomplished by the 3D Monte Carlo calculation code.

Let S be the signal (in pulses per second) received by a determined detector, and A the effluent's volume activity. The following relationship is then found:

$A = F \times S$

Transfer function F, expressed in $m^3$, relates the signal to the effluent's total activity.

The transfer function may be factorised as follows:

$F = [p(C/D) \times P(D/V_c) \times V_c]^{-1}$ where p(C/D) is the probability that the pulse is counted by the detector, bearing in mind that the particle has arrived at the detector (this probability represents the intrinsic detector efficiency);

$p(D/V_c)$ is the probability that a particle emitted in the volume of effluent contained in the tank arrives at the detector (this probability represents the geometric detector efficiency);

$V_c$ is the volume of effluent contained in the tank.

Probability $p(D/V_c)$ is very small, due to the short path of alpha particles in a liquid.

If $V_5$ is taken to be the "α particle emitted in the volume lower than or equal to the path of the α particles" event, and $V_{c-s}$ the "α particles emitted in the remainder of the volume of effluent" event, probability $p(D/V_c)$ becomes:

$P(D/V_c) = p(D/V_s) \times p(V_s) + p(D/V_{c-s}) \times p(V_{c-s})$

Although probability $p(V_{c-s})$ may be very great, probability $p(D/V_{c-s})$ is by definition zero.

The transfer function is then:

$F = [p(C/D) \times p(D/V_s) \times p(V_s) \times V_c]^{-1}$

Probability $p(D/V_s)$ that a particle is detected, bearing in mind that it has been emitted in volume $V_s$, defines the geometric efficiency related to the source volume.

Probability $p(V_s)$ is equal to the ratio of the volumes in the case of a uniform distribution of activity.

The 3D Monte Carlo calculation code enables magnitudes $p(V_s)$, $p(D/V_c)$ and $p(D/V_s)$ to be evaluated.

The detection efficiency (i.e. $p(C/D) \times p(D/V_c)$) can then be calculated by using the above formulae.

The physical-chemical characteristics of the volume of solution seen individually by each detector (such as the density, salinity, nature of the effluent (aqueous, organic, acid), etc.) must be taken into consideration in the Monte Carlo modelling in order to obtain a detection efficiency which is as close as possible to reality.

The measuring system's M alpha radiation detectors are connected to P measuring channels, where P is an integer greater than or equal to 1 and less than or equal to M. It will be considered that alpha radiation detectors which are connected by a single measuring channel have the same physical-chemical characteristics: detectors connected to a single measuring channel will therefore be calibrated identically. If each alpha radiation detector is connected to its own measuring channel each detector will be calibrated individually: it will then be possible to obtain a different calibration for each detector, enabling a calibration to be obtained which is as close as possible to the medium in which the measurement is made (clean or sludge phase).

To calculate signal S another element which must be determined is the number of channels over which the signal must be integrated. This element directly influences the detection efficiency value. This action enables the signal-to-noise ratio to be optimised.

For example, FIG. 1 represents the change of the signal-to-noise ratio (pulses measured by an alpha radiation semiconductor detector as a function of energy, if such a detector is dipped in water). Bearing in mind that most α particles have an energy of between 3000 and 7000 keV, the graph is produced between 0 and 7000 keV. The full squares represent the signal/noise ratio, while the solid-line curve represents the background noise measured by the detector. In the case of the detector shown in FIG. 1 when it is placed in water, it is observed that the background noise is minimal between 2000 and 4800 keV: to detect as many α particles in water as possible, whilst having a minimal signal/noise ratio, integration is therefore optimal between 3000 and 6000 keV. An accurate setting of the number of channels to be taken into account thus enables the detection efficiency to be optimised, and the detection limit to be reduced.

After calibration, the semiconductor detector(s) is/are used to measure the effluent's alpha activity.

In the context of the invention the calculation enabling total activity $A_T$ of an effluent to be determined is given by the following formula:

$$A_T = \sum_{j=1 \text{ à } M} A_j$$

where M is the number of alpha radiation detectors of the measuring system and $$A_j = \frac{N_j}{t \times V_j \times \varepsilon}$$

where $N_j = N_B - N_0$ where $N_j$ is the count without background noise (in pulses) measured by detector j, where $N_B$ is the raw count (in pulses) measured by detector j, where $N_0$ is the count of the background noise (in pulses) measured by detector j, where t is the count period (in seconds) of detector j, where $\varepsilon$ is the detection efficiency of detector j, and where $V_j$ is the volume seen by detector j.

Measurement $A_j$ obtained in this manner thus gives a value in Becquerel per $m^3$.

It should be noted that the raw count and background noise count periods must be identical for the above formula to be valid.

The number of alpha radiation detectors included in the measuring system according to the invention enables the performance of the measuring system to be improved in terms of detection limit. This number should be optimised in accordance with the measuring accuracy which it is desired to obtain, with the volume of effluent, and also with the number of identified different phases to be characterised (it is preferable in this case to have at minimum one detector for each different phase if permitted by the volume of effluent). For example, the greater the effluent volume, the higher must be the number of detectors in order to increase the accuracy of measurement of the activity.

Furthermore, apart from increasing measuring accuracy and determining the calibration coefficient to be used, it is also advantageous to have the alpha radiation detectors at different heights in the effluent in order to detect the presence of a gradient of activity, if the activity is not uniform throughout the effluent, for example in the case of a decantation. By positioning the measuring device's alpha semiconductor detectors at different heights in the tank, a satisfactory representativeness of alpha activity distribution in the tank is obtained. The measuring device's detection efficiency is then no longer determined in relation to the entire volume of the effluent, but for each section of effluent covered by each detector: instead of presuming that the distribution of alpha activity in the effluent is uniform, it is presumed in this case that the distribution of the alpha activity is uniform radially and across the full height of the section "seen" by each alpha semiconductor detector. It is also presumed that the density and chemical composition of the effluent are constant within a given section. This division into sections therefore enables any density gradients present in the tank to be determined and, above all, enables a measurement to be made in the tank bottom deposits with a specific detection efficiency. It is then possible to reduce the uncertainty concerning alpha activity, and better to determine the parameters influencing the determination of alpha activity, by reducing the random factors due to sample-taking.

The presence of a gradient in the tank is easily identified by the fact that the signal varies between the alpha radiation detectors when the alpha radiation detectors are identical and connected to different count channels (one count channel for each alpha radiation detector). This is the reason why it is preferable to use identical alpha radiation detectors.

This gradient, from the top to the bottom of the tank, may be due either to the decantation of the alpha emitters in the tank (which is valid above all in the case of aqueous active effluents, with neutral pHs), or to the decantation of the suspended matter present in the tank.

If the first case occurs the signal gradient will increase with the depth of the tank. In the second case this same gradient will be reduced. The combination of both effects counterbalances the gradient.

Thus, a positive gradient between two sections of effluent seen by two alpha radiation detectors positioned at different heights will be reflected in the Monte Carlo modelling by an increase of the emission rate, identical to the signal ratio obtained between these two sections.

In the case of a negative gradient, it will be the apparent density which will be increased in accordance with the signal ratio between the two sections.

In the case of a zero gradient the modelling of the section will be a compromise between these two effects.

In addition to the alpha radiation detector(s), the measuring system according to the invention may also include a detector responsible for determining the effluent's spectrometry, and thus for identifying the alpha emitter radioelements present in the effluent.

This detector dedicated to spectrometry of the effluent is a monocrystalline semiconductor detector, of the diamond CVD or SOI type. This detector is preferably located in the upper portion of the tank, i.e. in the cleanest portion of the effluent contained in the tank. The hypothesis that the isotope ratio between the different alpha emitter radioelements is constant throughout the tank is made. The diamond monocrystalline or SOI detector must also have a minimum diameter of 1 inch, in order to have a detection limit compatible with the tank's activity (detection limit of the order of 100000 Bq per $m^3$ in the case of α particles having energies ranging from 4 to 6 MeV).

As a first approximation, for each activity $A_j$ detected by the M alpha radiation detectors, the proportion of the activity for each alpha emitter radioelement may then be determined:

$$A_n = \%_n \times A_j$$

where $A_n$ is the alpha activity of alpha emitter radioelement n and $\%_n$ is the proportion of radioelement n in the effluent relative to the other alpha emitter radioelements.

Proportion $\%_n$ is determined from the spectrum obtained by the spectrometry detector according to the following ratio:

$$\%_n = N_n/N_T$$

where $N_n$ is the signal obtained by radioelement n (by the habitual techniques of spectrum deconvolution) and $N_T$ is the signal obtained in the spectrum zone containing all the alpha emitter radioelements (i.e. for the number of channels used for determining the isotopic information).

The proportion of total activity for each alpha emitter radioelement may also be determined directly using the following formula:

$$A_n = \%_n \times A_T$$

However, the measurement obtained in this manner will be accurate provided there is no gradient, or only a small gradient, in the effluent's activity.

FIG. 2 represents a tank 1 containing an effluent having three different phases 2, 3, 4 and in which an example embodiment of the measuring system according to the invention is introduced. In this example the measuring system includes five alpha radiation detectors 5 (represented by rectangles containing a cross), held in the effluent by a tree-shaped holding means 7, i.e. with a central shaft and branches. In this case, alpha radiation detectors 5 are connected to five measuring channels 6, one for each detector, and the five measuring channels 6 are connected to an adding means (not represented) (for example, a multi-channel analyser, a scaler, etc.). In this example, alpha radiation detectors 5 are positioned at the ends of the branches of the shaft, and are thus held at determined heights in the effluent. In particular the effluent in this case includes three different phases: a clear phase located in the upper part of the tank, and in which three alpha radiation detectors are located, a cloudy portion, in which one alpha radiation detector is located, and a sludge phase, in which one alpha radiation detector is located.

The holding means are preferably designed to allow the passage of various wires of use for satisfactory operation of the detectors (high-voltage and low-voltage power, signal transmission, etc.). In this example the structure of the shaft is hollow and is used for the passage of various wires.

In this case the detectors are inserted in the ends of the branches, such that only the active portion of the detectors is in contact with the effluent.

The shaft is preferably sealed and resistant to acid or basic compounds.

In this example embodiment the holding means are a shaft, but all means enabling the alpha radiation detector(s) to be held in a determined position in the tank are suitable. For example, the holding means may be a helical rod to which the alpha radiation detectors are attached.

The alpha radiation detectors are preferably located at some distance from the edges of the tank, in order to facilitate their calibration, by avoiding the requirement to take account of "edge effects".

According to another example embodiment of the measuring system according to the invention, 3 $m^3$ of active effluent is contained in a tank 2.3 m high with a diameter of 1.3 m. For such a container a number of 10 alpha radiation detectors is optimum from the standpoint of the cost of the measuring system and performance of said measuring system (detection limit).

With such a measuring system an average of one measuring point at every 23 cm of tank height is obtained. This average must of course be weighted according to the characteristic points which it is desired to quantify. In particular, the detector at the greatest depth will be directly positioned in the decantation sludges, the following one in the cloudy phase located above the sludges, etc.

A first study of this tank, and above all of its contents, enables the number of different phases present in the tank to be determined. The tank's filling and salinity are, for example, monitored inline by a level indicator and a salinity measurement.

When it has been filled with all the effluent to be analysed the level of the tank determines which detectors must be activated, i.e. which detectors are completely immersed in the effluent, and the salinity is an indicator of the apparent density to be entered into the 3D modelling in order to perform the digital calibration of the detectors. The result of this digital calibration provides the detection efficiencies of the ten detectors, which are therefore applied to them individually. In the case of active, non-acid effluents, use of PIPS-type semiconductor detectors is possible, on the express condition that the tank or detector is opaque to daylight. If this is not the case, or in the case of tanks with high pHs, detectors of the diamond SOI or polycrystalline or monocrystalline CVD type must be used.

Other example embodiments are described below.

According to a first example embodiment the measuring system includes ten alpha radiation detectors, of the diamond SOI type or CVD type, positioned in a tank, and ten independent measuring channels, where each measuring channel is associated with an alpha radiation detector. The ten measuring channels are connected to an unrepresented adding means. The alpha radiation detectors are spaced relative to one another vertically in the tank, such that the different phases of the effluent can be measured.

According to a second example embodiment, represented in FIG. 3, the measuring system is dipped in a tank 1 containing an effluent having three different phases 2, 3, 4. The measuring system includes, as in the previous example, ten alpha radiation detectors 5 (represented by rectangles including a cross), of the diamond SOI type or of the CVD type. It also includes a monocrystalline detector 15, of the diamond CVD or SOI type, dedicated to spectrometry of the effluent (represented by a rectangle including a circle). There are eleven independent measuring channels 6 and 16, one for each detector, and the ten measuring channels 6 connected to alpha radiation detectors 5 are connected to an unrepresented adding means. The detector dedicated to spectrometry 15 is placed in the upper portion of tank 1, i.e. in the portion of the effluent containing the least suspended matter. It is stipulated that the holding means are not represented in FIG. 3.

Figure 4:
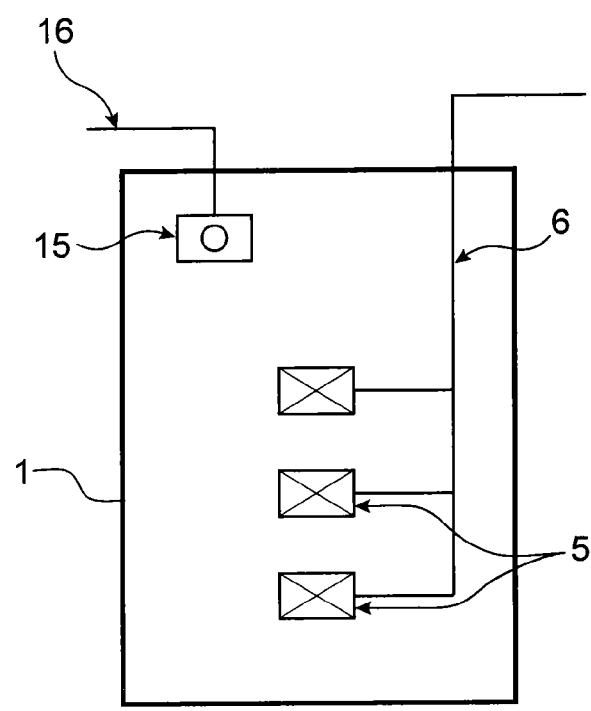
FIG. 4 represents another example embodiment of the measuring system according to the invention.

According to a third example, represented in FIG. 4, a measuring system is produced which is suitable to quantify the alpha activity of an effluent contained in a container of several hundred cm$^3$. For example, container 1 is a flask of the SG500 type measuring 8 cm high and 9 cm in diameter. The measuring system includes, for example, three alpha radiation detectors 5, of the diamond SOI or CVD type, a monocrystalline CVD detector 15 dedicated to spectrometry, and two measuring channels (one measuring channel 6 for three alpha radiation detectors 5 and one measuring channel 16 for detector dedicated to spectrometry 15). The alpha radiation detectors are positioned at different heights in the flask. It is stipulated that the holding means are not represented in FIG. 4.

In the three examples above the choice between the diamond SOI detectors and the CVD detectors for the detectors to be used to quantify the alpha activity is made according to the container and according to the alpha activity to be quantified. Indeed, if it is desired to quantify effluents having an alpha activity of less than 18.6 M Bq/m$^3$ it is preferable for the semiconductor detectors to be polycrystalline detectors of the diamond SOI type having a minimum area of 1 inch$^2$ (i.e. 2.54 cm$^2$). In this case, the container (tank or flask) must be a container which is opaque to light, or alternatively the SOI detector must be made opaque to visible light.

Conversely, if it is desired to quantify effluents having a very high alpha activity, i.e. an activity of greater than 18.6 M Bq/m$^3$, the semiconductor detectors will preferably be polycrystalline detectors of the CVD type.

One of the advantages of the invention is that it applies equally to alpha emitter radioelements present in containers containing several cubic meters or several cubic centimeters of effluents, and to neutral, basic or acid effluents, and also to low, high or very high alpha activity levels.

Another advantage of the measuring system according to the invention and of the related measuring method is that they enable the alpha activity in effluent tanks to be measured at different levels of the tank and in all the phases present in the tank (clean solution and sludges). A more accurate measurement of the effluent's alpha activity is thus obtained, and the gradient of the effluent's alpha activity within the tank may be known.

The measuring system and the method according to the invention have many other advantages compared to the prior art.

Firstly, in the prior art the measurement is made on a sample of effluent and, in addition, only the clean phase of the effluent can be used. The risk is then that a distorted activity result will be obtained which is not representative of the effluent's real activity throughout the tank. With the measuring system and the related method according to the invention the representativeness of the alpha activity measurement is much closer to the real value.

Furthermore, by virtue of the measuring system according to the invention, the activity of the alpha emitter radioelements present in the effluent may be identified and monitored inline. It is also possible to determine distribution of activity at all levels of the tank, by virtue of measurement of activity for each uniform tank section.

In addition, the time required to obtain an alpha activity measurement is shorter than in the prior art (measurement directly in the tank replaces sampling, transport and analysis of the sample).

In addition, shipments of nuclear materials are eliminated: in the prior art each sample taken requires that a nuclear shipment is made, and is then subject to special management as nuclear material.

Finally, with an in situ measuring method more frequent material monitoring may be undertaken than with an offline method.

The invention claimed is:

1. An in situ system for nuclear measurement of alpha radiation of an effluent, comprising:
M alpha radiation detectors, configured to be immersed in the effluent, and to measure directly alpha radiation emitted by the effluent, wherein M is an integer greater than or equal to 2, and wherein the M alpha radiation detectors are diamond semiconductor detectors obtained by chemical vapour deposition, or silicon semiconductor detectors covered with a diamond layer; and
P measuring channels connected to the M alpha radiation detectors, wherein P is an integer greater than or equal to 1 and less than or equal to M, and wherein each of the P measuring channels is configured to supply an alpha activity value or a sum of such values from the M alpha radiation detectors to which they are connected,
wherein the system is configured to add together the value or values supplied by the P measuring channels,
wherein the M alpha radiation detectors are individually calibrated by an alpha particle transport code based on Monte Carlo method,
wherein alpha radiation detectors of the M alpha radiation detectors which are connected to a given P measuring channel are calibrated in a same manner, and
wherein the effluent includes Q different phases, Q being an integer greater than or equal to 2, and at least two of the M alpha radiation detectors are positioned in different phases of the effluent.

2. The system according to claim 1, wherein P is equal to M.

3. The system according to claim 1, comprising at least one of the M alpha radiation detectors for each phase of the Q different phases.

4. The system according to claim 1, wherein the M alpha radiation detectors are identical.

5. The system according to claim 1, further comprising a monocrystalline semiconductor detector, as a spectrometry detector, configured to be immersed in the effluent, and configured to identify and quantify at least a proportion of alpha radiation emitter elements present in the effluent.

6. The system according to claim 5, wherein the monocrystalline semiconductor detector is a diamond chemical vapour deposition detector or a silicon-on-insulator semiconductor detector.

7. An in situ system for nuclear measurement of alpha radiation of an effluent, comprising:
M alpha radiation detectors, configured to be immersed in the effluent, and to measure directly alpha radiation emitted by the effluent, wherein M is an integer greater than or equal to 2, and wherein the M alpha radiation detectors are diamond semiconductor detectors obtained by chemical vapour deposition, or silicon semiconductor detectors covered with a diamond layer; and
P measuring channels connected to the M alpha radiation detectors, wherein P is an integer greater than or equal to 1 and less than or equal to M, and wherein each of the P measuring channels is configured to supply an alpha activity value or a sum of such values from the M alpha radiation detectors to which they are connected,
wherein the system is configured to add together the value or values supplied by the P measuring channels,
wherein the M alpha radiation detectors are individually calibrated by an alpha particle transport code based on Monte Carlo method,
wherein alpha radiation detectors of the M alpha radiation detectors which are connected to a given measuring channel are calibrated in a same manner, and
wherein an M alpha radiation detector among the M alpha radiation detectors is monocrystalline, and is connected to a first measuring channel, chosen from among the P measuring channels, which supplies said value or values and is connected to a second measuring channel, different from the P measuring channels, which provides spectrometry of the effluent.

8. The system according to claim 7, wherein P is equal to M.

9. The system according to claim 7, wherein the effluent includes Q different phases, Q being an integer greater than or equal to 2, and at least two alpha radiation detectors of the M alpha radiation detectors are positioned in different phases of the effluent.

10. The system according to claim 9, comprising at least one alpha radiation detector of the M alpha radiation detectors for each phase of the Q different phases.

11. The system according to claim 7, wherein the M alpha radiation detectors are identical.

12. The system according to claim 7, further comprising a monocrystalline semiconductor detector, as a spectrometry detector, configured to be immersed in the effluent, and configured to identify and quantify at least a proportion of alpha radiation emitter elements present in the effluent.

13. The system according to claim 12, wherein the monocrystalline semiconductor detector is a diamond chemical vapour deposition detector or a silicon-on-insulator semiconductor detector.

14. The system according to claim 12, further comprising a holder configured to hold the M alpha radiation detectors immersed at determined positions in the effluent, and wherein the spectrometry detector is attached to the holder.

15. The system according to claim 7, further comprising a holder configured to hold the M alpha radiation detectors immersed at determined positions in the effluent.

16. The system according to claim 15, wherein the holder is configured to hold at least two alpha radiation detectors of the M alpha radiation detectors at different heights in the effluent.

17. The system according to claim 15, wherein the holder comprises a shaft including branches on which the M alpha radiation detectors are positioned.

18. A method for in situ nuclear measurement of alpha radiation of an effluent, comprising:
immersing in the effluent M alpha radiation detectors configured to measure directly alpha radiation emitted by the effluent, wherein M is an integer greater than or equal to 1, wherein the M alpha radiation detectors are diamond semiconductor detectors obtained by chemical vapour deposition, or silicon semiconductor detectors covered with a diamond layer, wherein the M alpha radiation detectors are connected to P measuring channels, wherein P is an integer greater than or equal to 1 and less than or equal to M;
calibrating the M alpha radiation detectors by an alpha particle transport code based on Monte Carlo method, wherein alpha radiation detectors of the M alpha radiation detectors which are connected to a given measuring channel are calibrated in a same manner;
detecting P values of the alpha radiation using the P measuring channels connected to the M alpha radiation detectors, wherein an $i^{th}$ value detected (where i=1 to P) is equal either to a value resulting from a single M alpha radiation detector, if the corresponding P measuring channel is connected only to the single M alpha radiation detector, or to a sum of values from alpha radiation detectors of the M alpha radiation detectors connected by a measuring channel of the P measuring channels; and
adding together the detected value or values,
wherein the effluent includes Q different phases, Q being an integer greater than or equal to 2, and at least two alpha radiation detectors of the M alpha radiation detectors are immersed in different phases of the effluent.

19. The method according to claim 18, wherein the M alpha radiation detectors are positioned at different heights in the effluent.

20. The method according to claim 18, further comprising performing a spectrometry of the effluent to identify and quantify at least a proportion of alpha radiation emitter elements present in the effluent.

21. The method according to claim 20, wherein the performing the spectrometry of the effluent comprises immersing a monocrystalline semiconductor detector, or a silicon semiconductor detector covered with a diamond layer, in the effluent, and detecting values supplied by the monocrystalline semiconductor detector or the silicon semiconductor detector covered with the diamond layer.

* * * * *